US 6,524,846 B1

(12) United States Patent
Robinson, Jr.

(10) Patent No.: US 6,524,846 B1
(45) Date of Patent: Feb. 25, 2003

(54) BIOLOGICAL TOXIN DETECTION SYSTEM FOR MAILED MATERIALS

(76) Inventor: William L. Robinson, Jr., 2517 Quantico Ave., Baltimore, MD (US) 21215

( * ) Notice: Subject to any disclaimer, the term of this patent is extended or adjusted under 35 U.S.C. 154(b) by 45 days.

(21) Appl. No.: 09/985,520

(22) Filed: Nov. 5, 2001

(51) Int. Cl.[7] ................................................. C12M 1/34
(52) U.S. Cl. .............................. 435/287.4; 435/288.7; 435/287.7; 436/111; 422/86
(58) Field of Search ........................... 422/56, 58, 86, 422/87; 436/111–113; 435/287.4, 287.7, 288.7

(56) References Cited

U.S. PATENT DOCUMENTS 4,205,043 A * 5/1980 Esch et al. .................. 116/206
4,258,000 A * 3/1981 Obermayer ................. 116/206
4,840,919 A * 6/1989 Attar ........................... 422/57

* cited by examiner

Primary Examiner—David A. Redding
(74) Attorney, Agent, or Firm—Peter Gibson

(57) ABSTRACT

Envelopes and other containers intended for mail transportation possess a biological agent/toxin indicator operative upon the interior in detection of volatile bases including gaseous amines released from bacterial biological agents including *Bacillus antracis,* i.e. anthrax. The biological agent indicator has an acidic acid-base indicator compound that irreversibly changes color when neutralized by volatile bases. The compound is applied in liquid form to an appropriately porous substrate. A polymeric matrix is specifically suggested for this substrate. Irreversible indication of the presence of volatile bases including amines produced by live bacterial agents as toxins at temperate ambient conditions down to below freezing is provided. An indicator compound having a pH of 2–5 is recommended. Halogenated xanthene, sulphonated azo, and sulphonated hydroxy-functional triphenylmethane dyes are suggested. The presence of toxins produced by live bacterial biological agents within a package or container upon which the indicator is mounted is indicated by a slowly reversible color change. Primary public use envelopes and collection containers, secondary transportation and stationary quarantine enclosures, and articles worn inside a room with mail and when handling mail including a badge and gloves are specifically suggested.

23 Claims, 4 Drawing Sheets

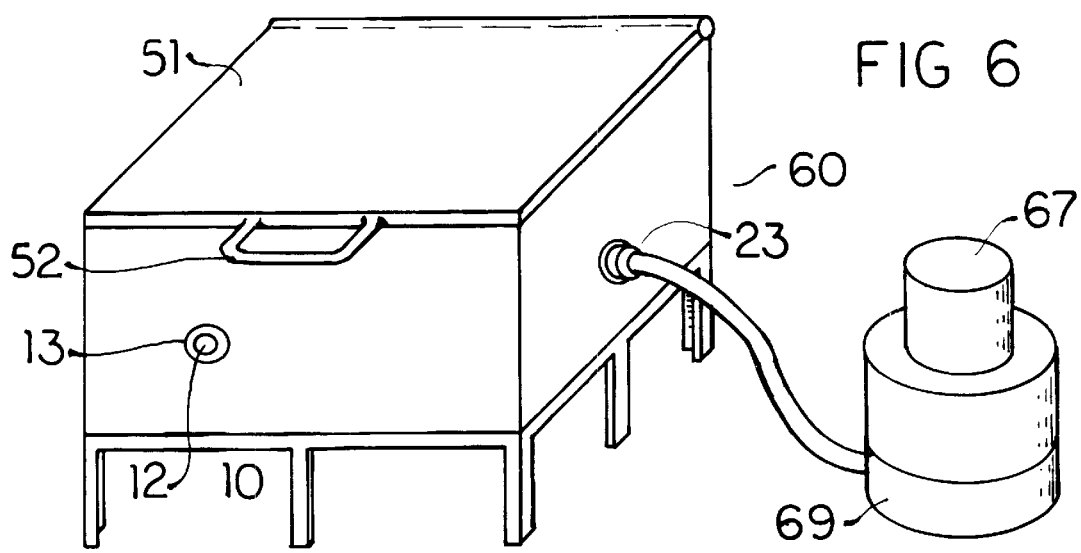
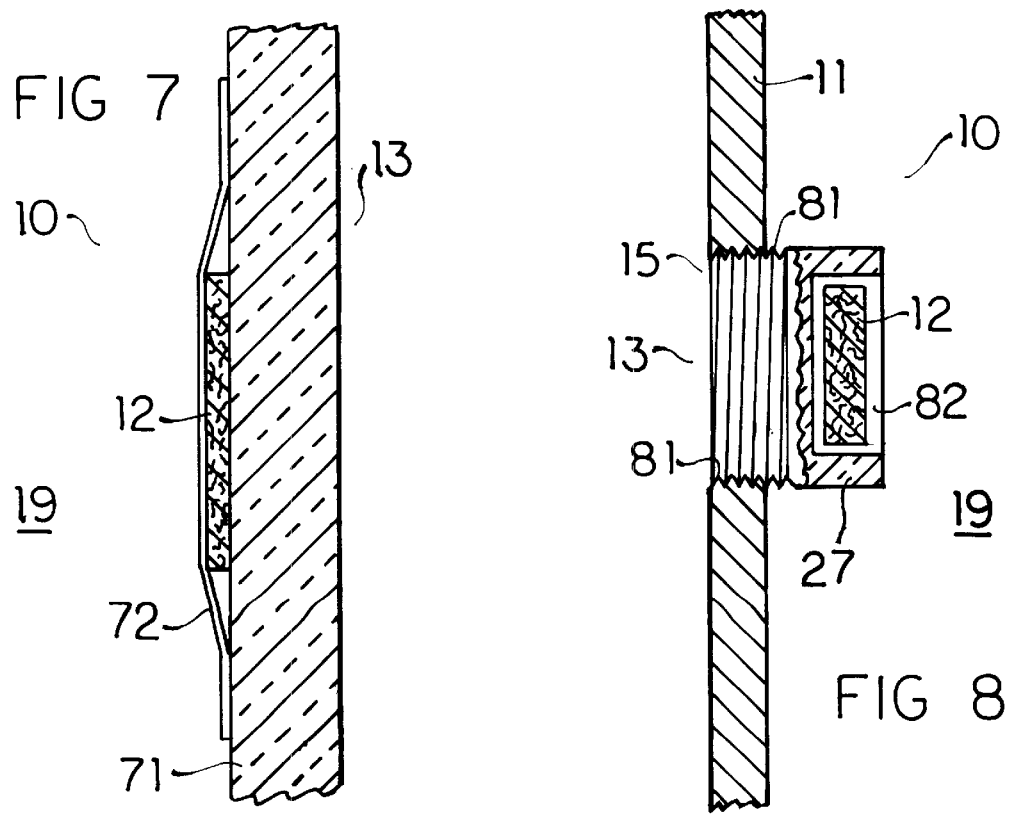

BIOLOGICAL TOXIN DETECTION SYSTEM FOR MAILED MATERIALS

BACKGROUND OF THE INVENTION

1. Field of the Invention

The present invention relates generally to anti-terrorism, more particularly to anti-terrorism measures for safeguarding the mail, and most specifically to safeguarding the mail from transmission of bacterial biological agents including *Bacillus antracis,* i.e. anthrax.

2. General Background

The specific problem addressed herein first came to the attention of the public in early October 2001 when the first case of mail transferred anthrax infection became known which was only several weeks after the terrorist destruction of the world trade center in New York City on Sep. 11, 2001. In the second month following this it became publicly apparent that anthrax bacteria was being sent through the U.S. Mail as confirmed by the deaths of several U.S. Postal Service (U.S.P.S.) employees from anthrax infection. Anthrax is contracted by cutaneous contact or inhalation of spores. *Clostridium botulinum* is primarily contracted by ingestion. Bubonic plague is caused by a bacterium of the genus Pasteurella and is contracted by both cutaneous contact and inhalation as is *Mycobacterium tuberculosis.* All of these bacterial biological agents have been recognized as current or potential terrorist weapons readily deployed through the mail.

Smallpox has also been recognized as a potential terrorist weapon that could also be deployed through the mail but is a virus and although it has been decades since smallpox vaccinations were administered on a large scale the vaccine is known to be quite good, i.e. relatively benign and easily administered in a single step. Smallpox vaccine was administered to six and a half million people, virtually the entire population of New York City, in the last public outbreak of smallpox in the United States in 1947 with only a handful of deaths resulting from the vaccination and fewer deaths from the outbreak. The only known vaccine for anthrax, in contrast, is considered problematic. The vaccine has been known for several decades but was only approved by the Federal Drug and Food Administration during the time discussed above in which mail borne anthrax infection became publicly known.

The anthrax vaccination currently available is publicly known to contain impurities from which side effects result. The vaccination, moreover, is not accomplished in a single step but requires four different inoculations months apart from each other and hence cannot be readily administered to anyone in a relatively brief amount of time. It is considered that vaccinations, which in principle rely upon the development of antibodies by the human body in reaction to a very small amount of the biological agent addressed, are inherently better suited to guard against viral rather than bacterial infections. Bacterial infections are typically combated with antibiotics, which are ineffective against viruses, and viruses are typically combated with vaccination. Every late fall or early winter there is typically a new strain of influenza virus for which a vaccine is developed and administered to people requesting the same.

STATEMENT OF NEED

Anthrax is particularly virulent and lethal because by the time that infection is manifest antibiotics are relatively ineffective. Without either a vaccine which can be safely and readily administered to large numbers of people or diagnosis early enough to enable effective treatment with antibiotics it is considered that anthrax, and other similar biological agents which can be contracted by contact or inhalation, presents a very serious terrorist weapon readily deployed through the mail and therefore a poignant need exists for an effective means of preventing such infection by means of this vector.

SUMMARY OF THE INVENTION

Objects of the Invention

A primary object of the present invention is the prevention of transmitting bacterial biological agents including *Bacillus antracis,* i.e. anthrax, through the mail.

A first ancillary objective of the present invention is a system for ensuring that mail does not contain biological agents including *Bacillus antracis,* i.e. anthrax.

A first auxiliary objective of the present invention is a means of recognizing mail as containing biological agents including *Bacillus antracis,* i.e. anthrax, without opening that mail.

A second ancillary objective of the present invention is means of recognizing mail containing biological agents including *Bacillus antracis,* i.e. anthrax, before handling that mail.

A second auxiliary objective of the present invention is a quarantine means for placing mail in quarantine during transportation.

A third auxiliary objective of the present invention is a quarantine means for placing mail in quarantine during storage.

Principles Relating to the Present Invention

In achievement of the above stated objectives it is considered that packaging and containers for mail be equipped with means of indicating the presence of bacterial biological agents including *Bacillus antracis,* i.e. anthrax, within that mail. It is suggested that an acidic acid-base indicator compound which changes color, when neutralized by volatile bases including gaseous amines produced by live bacteria, be utilized for visual indication. The indicator compound must be in communication with the interior of the package or container but must be read from the outside without opening the package or container which must further provide an effective seal against leakage of any bacteria therein. Paper is sufficient to provide this seal if a full enclosure is obtained and plastic, metal, and other materials are perfectly satisfactory in providing a sufficient seal if a full physical enclosure is effected.

An otherwise conventional paper envelope with a substantially transparent clear panel with an indicator disposed interiorly thereupon is suggested for primary public use. The indicator preferably is made from acidic acid-base indicator solution having a pH of 2–5 disposed upon an appropriately porous substrate. A polymeric matrix, particularly including alkoxysilanes, is specifically recommended which is readily manufactured in thin sheets and readily adheres to paper and other plastics including glassine, Cellophane™, and polyethylene which are specifically suggested for the clear panel. But the substrate can be paper, cotton, string, or any moderately porous material of essentially neutral color which will not obscure the change in color of the indicator solution therein caused by pH neutralization resulting from exposure to gaseous amines produced by live bacteria. The change in color is substantially irreversible, reversal requires weeks in an amine free environment, and will occur in moderate ambient temperatures down to below freezing if an appropriate indicator solution is utilized.

The rate of response and detection sensitivity of the indicator solution is improved by use of non-volatile acids and other components including concentrated sulfuric acid, sulfamic acid, phosphoric acid, zeolites, alumina, polyacrylic acid and suphonated perfluoroethylene. Preferred acidic acid-base indicators include: halogenated xanthene dyes, e.g. Phloxine B, Rose Bengal; Erythorsins; sulphonated azo dyes, e.g. Congo Red, Metanil Yellow; and sulphonated hydroxy-functional triphenylmethane dyes, e.g. Bromophenol Blue, Bromocresol Green, Phenol Red. Satisfactory operation below freezing is considered to be highly desirable and substantial irreversibility of the color change is considered necessary.

With further regard to an envelope providing a visual indication of live bacteria therein it is considered that such envelopes, and all other mail packaging including boxes which are intended for use by the public in enclosing material to be mailed, further preferably possess a means of verifying authenticity which is preferably invisible to humans but machine readable. A thin film plastic with magnetically stored information is suggested as are other authenticity means commonly deployed upon currency. Electronic fingerprints or 'watermarks' read by scanning devices embedded in a plastic window to which the substrate is affixed is specifically recommended. The objective is to avoid fraudulent imitation of the envelope or packaging.

It is also considered that, since an envelope or package deposited with the postal service might not possess a bacterial biological agent/toxin indicator and/or may not be properly sealed, it is desirable to detect the presence of bacterial biological agents/toxins in a container in which mail is deposited. This includes deposit boxes or collection containers colloquially known as mail boxes. These containers are typically steel enclosures with a hinged door weight biased shut through which letters and packages up one pound in the U.S. are legally deposited with the U.S.P.S. It is suggested that an indicator utilizing an acidic acid-base indicator solution deposed thereupon and thereby coated be positioned upon a wall of the container. Rather than a thin sheet however, it is suggested that a substantially transparent pane of rigid plastic or glass be utilized to provide the visibility of the indication element interiorly disposed behind this window.

It is similarly suggested that containers for transportation and storage of mail which provide a full enclosure of the same, be equipped with a bacterial biological agent/toxin indicator located behind a rigid substantially transparent window in a wall so that the mail held therein is effectively held in quarantine. It is further suggested that these quarantine containers also possess a substantially airtight seal and at least one air port by which a negative pressure with regard to ambient can be applied to the interior. The application of negative pressure will induce the release of any bacterial biological agents and toxins from envelopes and packages and enable detection of the same which otherwise might not be detected.

Disposition of a substrate coated with acidic acid-base indicator solution upon an article intended to be worn by U.S.P.S. employees is also suggested. A clip on style badge and gloves each bearing a bacterial biological agent/toxin indicator thereupon to be worn in a room containing mail, and/or when handling mail, are specifically recommended. It is also suggested that the substrate be comprised of threads which can be woven into the clothing intended to be worn by U.S.P.S. employees.

Details regarding the best known manner of construction and use of a system in accordance with the principles relating to the present invention may be appreciated with a reading of the discussion below, especially if made with reference to the drawings attached hereto and described briefly below.

BRIEF DESCRIPTION OF THE DRAWINGS

FIG. 6 is an isometric view of a storage container possessing a bacterial biological agent/toxin indicator in accordance with the principles relating to the present invention.

FIG. 7 is a cross sectional view taken from a side of a bacterial biological agent/toxin indicator in accordance with the principles relating to the present invention mounted on a transparent wall.

FIG. 8 is a plain elevational view taken from the top, partially cut away, of a bacterial biological agent/toxin indicator in accordance with the principles relating to the present invention.

Figure 1:
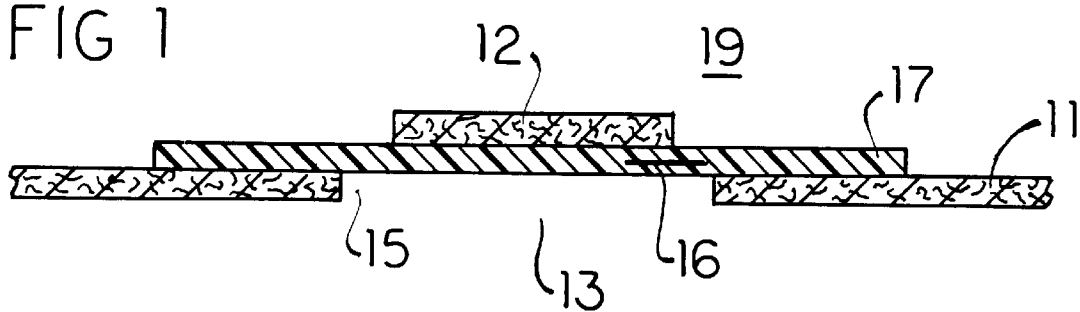
FIG. 1 is a cross sectional view taken from a side of a bacterial biological agent/toxin indicator in accordance with the principles relating to the present invention.

NOMENCLATURE 10 bacterial biological agent/toxin indicator
11 wall (of enclosure)
12 substrate (coated with acidic acid-base solution)
13 window
15 aperture through wall
16 electronic fingerprint
17 substantially transparent sheet material
19 interior (of enclosure)
20 envelope
21 front face
22 top edge
23 stamp
25 printed code 27 substantially transparent rigid material
30 box
40 mail receptacle
50 transportation container
51 lid
52 handles
53 port
60 storage container
67 vacuum
69 filter
71 substantially transparent wall
72 adhesive tape
81 threading
82 cavity
90 badge indicator
91 clip
92 adhesive
96 glove

DETAILED DESCRIPTION OF THE PREFERRED EMBODIMENT

A bacterial biological agent/toxin indicator 10 in accordance with the principles relating to the present invention is seen in FIG. 1 to be comprised of an appropriately porous substrate 12 coated with an acidic acid-base indicator solution disposed in the enclosure interior 19 behind, and preferably attached to, a piece of substantially transparent sheet material 17 covering an aperture 15 through a wall 11 of the enclosure to create a window 13 for viewing the substrate 12 from the exterior of the enclosure. The acidic acid-base indicator, as previously mentioned, preferably has a pH of 2–5 and changes color in a substantially irreversible manner, i.e. with reversal requiring at least a week in a amine free environment, in consequence of neutralization effected by volatile bases including gaseous amines released by live bacteria including Bacillus antracis, i.e. anthrax.

Also as mentioned previously, the rate of response and detection sensitivity, particularly with regard to use in temperate ambient conditions down to below the freezing point of water, of the indicator solution is improved by use of non-volatile acids and other components including, respectively, concentrated sulfuric acid, sulfamic acid, phosphoric acid; and zeolites, alumina, polyacrylic acid, sulphonated perfluoroethylene. Preferred acidic acid-base indicators include: halogenated xanthene dyes, e.g. Phloxine B, Rose Bengal; Erythorsins; sulphonated azo dyes, e.g. Congo Red, Metanil Yellow; and sulphonated hydroxyl-functional triphenylmethane dyes, e.g. Bromophenol Blue, Bromocresol Green, Phenol Red. More generally it is suggested, for obtainment of an appropriate acidic acid-base indicator solution, to avoid a water base or any other aqueous mediation and to otherwise optimize operation at lower temperatures and lower densities of volatile bases. Phloxine B and Bromophenol blue are specifically recommended.

Figure 2:
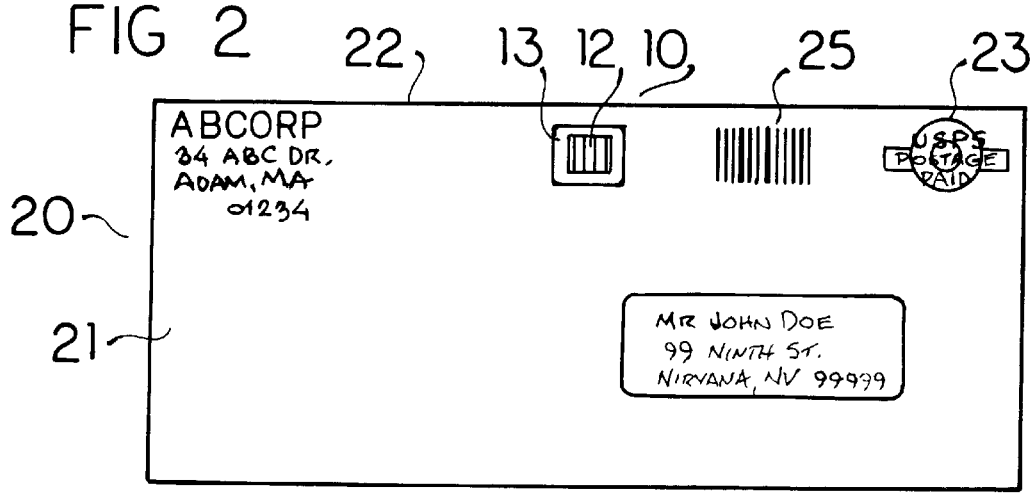
FIG. 2 is a plain elevational view taken from the front of an envelope possessing a bacterial biological agent/toxin indicator in accordance with the principles relating to the present invention.
Figure 3:
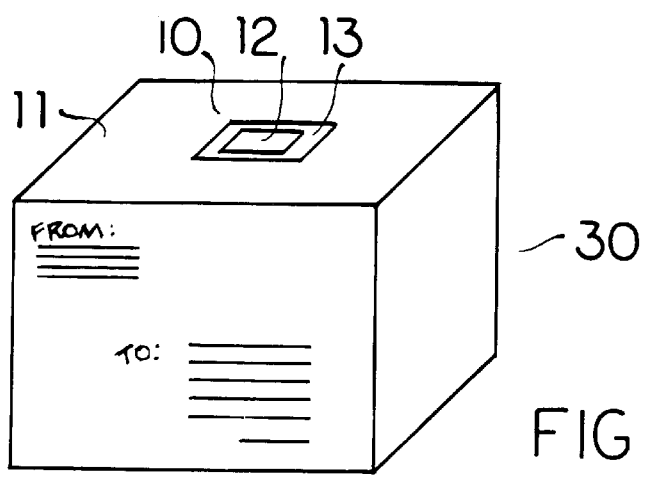
FIG. 3 is an isometric view of a package possessing a bacterial biological agent/toxin indicator in accordance with the principles relating to the present invention.

It is emphasized that this recommendation regarding the acidic acid-base indicator solution applied to the appropriately porous substrate 12 is primarily intended for primary public use envelopes 20 and other government approved containers specifically including corrugated paper boxes 30, respectively depicted in FIGS. 2 & 3, having a bacterial biological agent/toxin indicator 10 mounted thereupon in accordance with the principles relating to the present invention as these primary public use envelopes 20 and boxes 30 are expected to be used in conditions including temperatures down to below freezing. Other applications including that discussed below with regard to FIGS. 6 & 9–12 simply require a bacterial biological agent/toxin indicator 10 utilizing an acidic acid-base indictor solution which irreversibly changes color in consequence of neutralization effected by volatile bases including gaseous amines and other toxins released by live bacterial biological agents including Bacillus antracis, i.e. anthrax.

In the cases represented by FIGS. 1–5, 7 & 8 of the drawing sheets attached hereto a bacterial biological agent/toxin indicator 10 is mounted upon a wall 11 of an enclosure for materials deposited with the U.S.P.S. as mail in communication with the interior 19 of the enclosure and is visible from the exterior of that enclosure through an area of substantially clear material known herein as a window 13 which is contiguous with a wall 11 of the enclosure. As seen in FIG. 1, it is preferred that this window 13 have the substrate 12 coated with acidic acid-base indicator solution affixed directly thereto and that an electronic fingerprint 16 or 'watermark' comprised of magnetic or other material which contains electronic, i.e. digital, data equivalent to a code which is machine readable by scanning be affixed to, or most preferably as depicted, embedded in the substantially transparent sheet material 17 or other substantially clear material comprising the window 13. This use of an electronic fingerprint 16 ensures that the window 13 with the substrate 12 coated with acidic acid-base indicator solution affixed thereto is in place.

Envelopes 20 in accordance with the principles relating to the present invention are preferably made of paper for the same reason that conventional envelopes are so constructed: paper is inexpensive, opaque, lightweight, rigid, and easily folded and glued in construction of an envelope. The U.S.P.S., among other postal services, also relies extensively upon pneumatic handling of envelopes during processing as this facilitates orientation required of processing of individual envelopes in batch quantities. The machines and methods utilized for contemporary processing of U.S. Mail, in brief, are essentially predicated upon conventional construction of envelopes in paper within certain dimensions for automatic handling. 'Pre-sorted' business mail bearing U.S.P.S. 'POSTNET' bar codes and alphanumeric characters both read by optical scanners during automated processing is of particular concern with this regard.

It is recommended that for business mail envelopes 20 the bacterial biological indicator 10 be consistently located with regard to the overall envelope 20 configuration on the front 21 of the same as depicted in FIG. 2 preferably proximate the top edge 22 to facilitate reading of the same by an optical scanner during automated processing. Other envelopes 20 in accordance with the principles relating to the present invention must be sorted manually and it is unimportant as to where the bacterial biological agent/toxin indicator 10 is located except that it must be in communication with the interior 19 of the envelope 20 and visible from an exterior of the same.

It is noted that the envelope 20 may be constructed of substantially transparent or translucent material in which case the wall 11 concerned effectively provides a window 13. However, assuming an opaque paper wall 11 upon the envelope 20 and the need for a window 13 contiguous with the wall 11, it is recommended that the substrate 12 coated with acidic acid-base indicator solution be attached directly to the back side of the window 13. It is recommended that the window 13 be made of either a substantially transparent paper, cellulose, or plastic. Glassine, which is made from sulfite pulp which is extensively beaten and calendered is conventionally utilized for envelope windows generally and is specifically recommended. The substantially transparent sheet 17 covering an aperture 15 through a wall 11 comprising the window 13 seen in FIG. 1 is further preferably securely adhered to a margin about the periphery of the aperture 15 through the wall 11. It is preferred that this substantially transparent sheet 17 be adhered to the interior 19 face of the wall 11 as shown in FIG. 1 though the exterior face of the wall 11 could be used. This is considered primarily to be the most economic manner of construction available.

As an alternative material for a envelope 20 window 13 it is suggested that Cellophane™, a cellulose regenerated by Du Pont™ in thin sheets up to 0.0016" thick, possesses excellent transparency and is easily laminated with films of synthetic resin including a polymeric matrix specifically suggested for the substrate 12 of a bacterial biological agent/toxin indicator 10 coated with acidic acid-base indicator solution. Polyethylene is another material recommended for a substantially transparent sheet 17 in a window 13 of an envelope 20 in accordance with the principles relating to the present invention. Cellophane™ has greater transparency than polyethylene but lesser strength and chemical resistance.

Aside from envelopes 20 mailed materials are typically enclosed in corrugated paper walled boxes for essentially the same reasons that paper is preferred for conventional envelopes. A mailing box 20 in accordance with the principles relating to the present invention possesses a bacterial biological agent/toxin indicator 10 preferably possessing the above described construction as mounted upon a wall 11 of the box in communication with the interior 19 of the same and visible from the outside. It is preferred that the substrate 12 coated with acidic acid-base indication solution be directly adhered to the interior surface of a substantially transparent sheet 17 which is adhered with an overlapping margin about the periphery of an aperture 15 through the wall 11 in a similar manner as that recommended for an envelope 20 in accordance with the principles relating to the present invention and depicted in FIG. 1.

Figure 4:
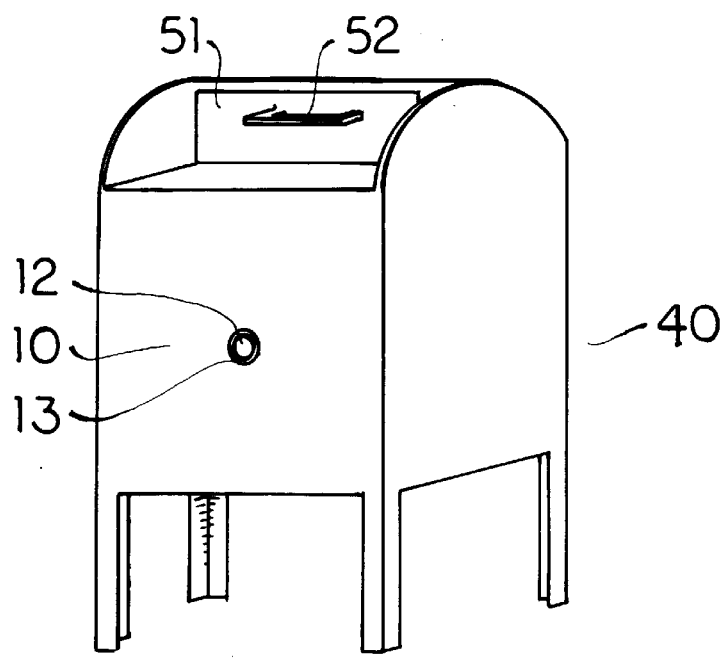
FIG. 4 is an isometric view of a collection container, i.e. mail receptacle, possessing a bacterial biological agent/toxin indicator in accordance with the principles relating to the present invention.

It is further considered that, while envelopes 20 and mailing boxes 30 possessing a bacterial biological agent/toxin indicator 10 in accordance with the present invention can be verified by means of a bar code 25, seen in FIG. 2, or magnetic strip containing a magnetically stored code, an electronic watermark, or other identifying code or mark which can be read by an optical or magnetic scanner, verified as genuine, and processed safely; prior to receipt of the mail at a processing facility it is possible that envelopes and boxes and even materials which are not held in a separate enclosure may be placed in a public mail receptacle 40, i.e. collection container, such as that depicted in FIG. 4 and that a bacterial biological agent/toxin indicator 10 mounted on a wall 11 of the mail receptacle 40 as seen therein for the primary purpose of detecting loose live bacteria, and toxins produced by the same, deposited therein.

In this case it is preferred that the substrate 12 coated with acidic acid-base indicator solution be disposed behind a window 13 comprised of a substantially transparent rigid material 27, preferably acrylic, mounted by appropriate means in an aperture 15 through a wall 11 of the mail receptacle 40. FIG. 8 depicts a window 13 comprised of a substantially transparent rigid material 27 shaped as a plug with exterior threading 81 threaded into an interior threading 81 of an aperture 15 through a metal wall 11 such as typically found in the construction of mail receptacle. The substrate 12 coated with acidic acid-base solution in this case is seen to reside in a cavity 82 of this plug shaped window 13, does not require adhesion to any structure in order to ensure visibility from the exterior through the window 13, and is readily replaced. This particular construction is considered to be well suited to both retrofitting of existing metal collection containers and other mail receptacles 40 and to any new metal mail containers including storage containers 50 discussed further below.

Figure 5:
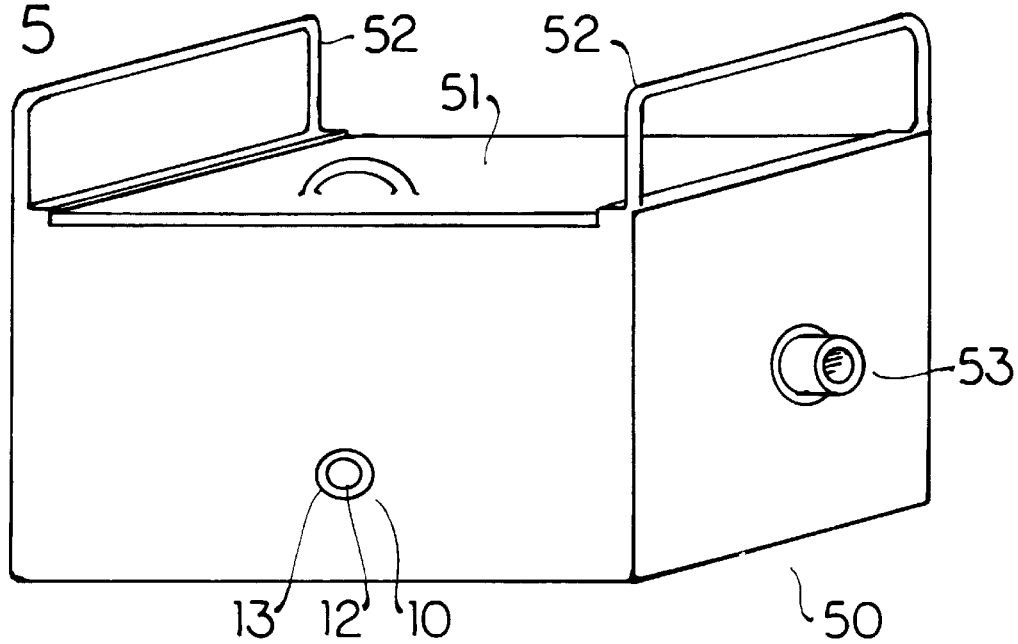
FIG. 5 is an isometric view of a transportation container possessing a bacterial biological agent/toxin indicator in accordance with the principles relating to the present invention.

It is considered that removal of mail from a mail receptacle 40 is necessary prior to inspection of mail contained therein and that it is desirable to quarantine all materials deposited with the U.S.P.S. prior to such inspection. For transportation of mail from mail receptacles 40 such as that shown in FIG. 4 it is hence suggested that a transportation container 50 as depicted in FIG. 5 be utilized which provides full enclosure and possesses a bacterial biological indicator 10 mounted upon a wall 11 with a substrate 12 coated with acidic acid-base solution in communication with the interior 19 and visible from the exterior through a window 13 which is preferably of rigid plastic. A lid 51 providing closure of an otherwise open top surface is suggested along with a pair of handles 52 to facilitate routine operation whereby mail from a mail receptacle is spilled into the open transportation container 50.

Upon arrival at a mail processing center it is considered that while envelopes 20 and mailing boxes 30 in accordance with the principles relating to the present invention can be visually inspected to ensure that there are no live bacterial biological agents including *Bacillus antracis,* i.e. anthrax, in that mail there may still be other types of mail which do not possess a bacterial biological agent/toxin indicator 10 and this mail, furthermore, may be properly sealed and hence may carry live bacterial biological agents which have not yet been released from enclosure and undetected by the bacterial biological agent/toxin indicators 10 upon either the mail receptacle 40 or the transportation container 50. Prior to arrival at a mail processing center, moreover, manual contact with this mail by U.S.P.S. employees can be avoided. The mail can be removed from the mail receptacle 40 and transferred by gravity into a transportation container 40 with a rake and the transportation container emptied by opening the lid 51 and inverting the same, preferable over a storage container 60 possessing a bacterial biological indicator 10 mounted upon a wall 11 as depicted in FIG. 6.

It is suggested that the storage container 60 possess an opening with a closure that effects a substantially airtight seal and that means of agitating the contents and/or applying a negative pressure to the interior 19 of the storage container 60 be utilized to cause any loose live bacterial biological agents which might be released from the mail during processing to be released inside the storage container 60 and detected by the bacterial biological agent/toxin indicator 10 mounted upon a wall 11 of the same. And it may be desirable to perform this operation upon the transportation container 50 also for which reason a port 53 can be provided upon a wall 11 as seen in FIG. 5. A vacuum 67 and filter 69 are connected to the port 53 seen on one wall 11 of the storage container 60 seen in FIG. 6 to provide negative pressure and safe removal of biological agents from mail contained in the interior 19.

It is recognized that in all likelihood all mail will soon be irradiated as soon as possible after arrival at a mail processing center and that this irradiation will kill virtually all pathogens which may be in that mail including any bacteria. Use of envelopes 20, mailing boxes 30, mail receptacles 40, transportation containers 50, and storage containers 60 each equipped with a bacterial biological agent/toxin indicator 10 as discussed above will safeguard U.S.P.S. employees prior to irradiation of the mail as any loose live bacteria released from the mail will be detected before it is handled. This system, moreover, facilitates tracking of any bacterial biological agents deposited with the postal service.

It is emphasized that the primary public use enclosures, e.g. envelopes 20 and mailing boxes 30 possessing bacterial biological indicators 10 as described above, are considered the most important element in the comprehensive system also including mail receptacles 40, transportation containers 50, and storage containers 60 all preferably possessing bacterial biological agent/toxin indicators 10. Only the envelopes 20 and mailing boxes 30 provide direct clues as to the identity of terrorists responsible for attempting to utilize the mail for transmission of bacterial biological agents. The public mail receptacles 40 indicate location of the same lacking any direct clues upon the envelope but without the envelopes 20 and mailing boxes 30 possessing bacterial biological agent/toxin indicators 10 it is considered virtually impossible to quickly identify and isolate a particular piece of mail as the specific vector utilized by the terrorists.

With regard to construction of envelopes 20 and mailing boxes 30 an essentially conventional approach utilizing paper and corrugated paper was suggested above. In particular, with reference to the construction depicted in FIG. 1, it was suggested that the appropriately porous substrate 12 coated with acidic acid-base solution be affixed to the interior surface of the substantially transparent sheet material 17 used in the window 13. It is considered that while this approach is considered wholly appropriate to envelopes 20 it is rather less satisfactory for mailing boxes 30 and obviously unsuited to metal walled mail receptacles 40 or storage containers 60. Use of a substantially transparent rigid material 27, preferably acrylic, and a specific means of construction utilizing a threaded plug style window 13 with an interiorly disposed cavity 82 as represented in FIG. 8 has been suggested for these metal walled containers 40, 60.

With particular regard to a transportation container 50 in accordance with the principles relating to the present invention it is considered that the entire enclosure can be molded in substantially transparent material such as acrylic sheet and that, in this case, the window 13 is comprised of the wall 11 itself. This approach is depicted in FIG. 7 wherein it is seen that the appropriately porous substrate 12 coated with acidic acid-base indicator solution is attached directly to the interior surface of the substantially transparent wall 71, in this case with two pieces of conventional adhesive tape 72. The porous substrate 12 coated with acidic acid-base indicator solution is preferably quite thin, approximately 0.010" being considered sufficient, and it is considered desirable to easily apply and remove the same from multiple locations of a transportation container 50.

It is also considered that, in both protection of U.S.P.S. employees and identification of mail carrying bacterial biological agents, it is desirable to have a bacterial biological indicator wearable by U.S.P.S. employees inside mail rooms in which contamination by bacterial biological agents is suspected. In this case the enclosure involved is typically the room in which mail is handled. Even if envelopes 20, mailing boxes 30, mail receptacles 40, transportation containers 50, and storage containers 60 all in accordance with the principles relating to the present invention are utilized and the mail concerned handled with tools to avoid direct human contact with that mail, the threat of airborne spores of *Bacillus antracis* being released and causing 'cross contamination' is considered quite possible.

Figure 9:
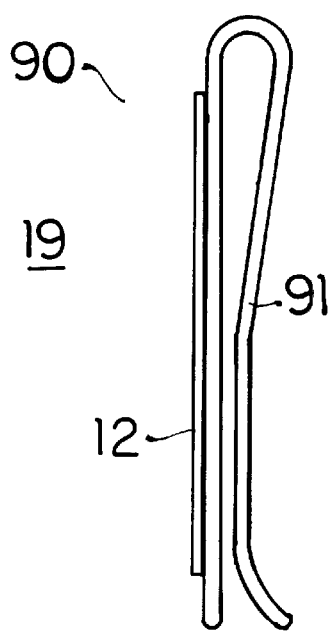
FIG. 9 is plain elevational view taken from a side of a clip on style badge bacterial biological agent/toxin indicator in accordance with the principles relating to the present invention.
Figure 10:
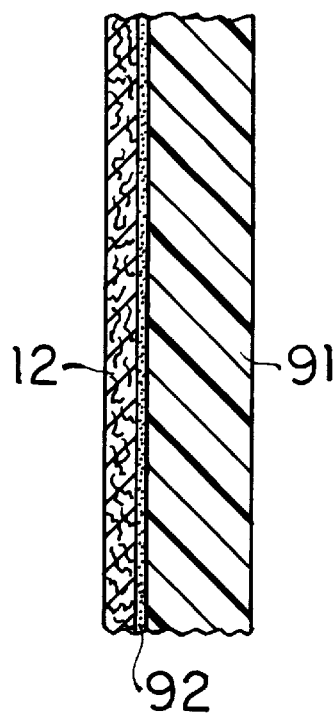
FIG. 10 is a cross sectional detail view of the construction utilized in the bacterial biological agent/toxin indicator depicted in FIG. 9.

The badge indicator 90 depicted in FIG. 9 is intended to be worn by U.S.P.S. employees to detect airborne bacterial biological agents including *Bacillus antracis*. A substrate 12 coated with acidic acid-base indicator solution is affixed to a rigid structure comprised, in the case shown, of a clip 91 so that the badge indicator 90 can be worn on a shirt pocket or other convenient location disposed in contact with the interior 19 of the mail room, preferably in between the mail an employee is handling and the mouth and nose of that employee, as it is inhalation of airborne spores of Bacillis antracis which is primary concern in this case. It is suggested that the clip 91 be made of a thermoplastic, as seen in FIG. 10, and that the substrate 12 coated with acidic acid-base indicator solution be affixed by adhesive 92 as depicted.

Figure 11:
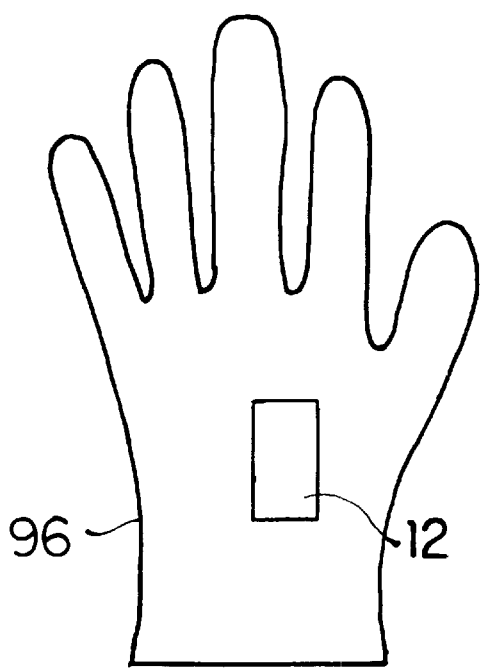
FIG. 11 is a plain elevational taken from the top of a glove with a bacterial biological agent/toxin indicator in accordance with the principles relating to the present invention.
Figure 12:
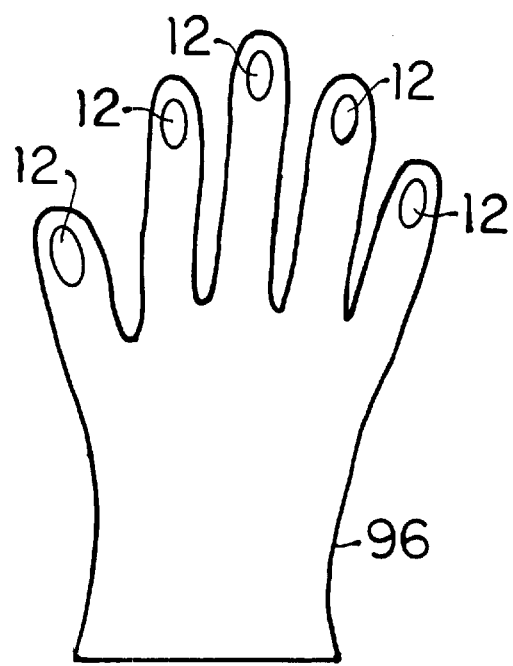
FIG. 12 is plain elevational taken from the bottom of a glove with a bacterial biological agent/toxin indicator in accordance with the principles relating to the present invention on each glove finger.

In order to avoid direct contact with mail containing bacterial biological agents including *Bacillus antracis* by U.S.P.S. employees and to facilitate identification of this mail it is also suggested that gloves 96 having at least one exteriorly mounted substrate 12 coated with acidic acid-base indicator solution as seen in FIGS. 11 & 12 be worn. The glove 96 seen in FIG. 11 has one substrate coated with acidic acid-base indicator on the top of the hand, where it is most easily seen by the U.S.P.S. employee wearing the same. The glove 96 seen in FIG. 12 has five substrates 12 coated with acidic acid-base indicator solution, one substrate 12 on each finger tip, which are each disposed upon the bottom or palm side of the glove 96 where contact is most likely to be made with a bacterial biological agent including *Bacillus antracis* contained in or otherwise carried by mail being handled manually.

It is commented that generally the appropriately porous substrate 12 coated with acidic acid-base indicator solution may simply consist of a strip of paper, cotton, flax, string or thread, low density porous polymeric matrix or any other suitable material. It is suggested that natural or synthetic fibers woven into clothing for wearing in mail rooms and other enclosures containing mail comprise the substrate 12 coated, and/or impregnated, with acidic acid-base indicator solution so that the article of clothing becomes a bacterial biological agent/toxin indicator 10. The porosity and thickness of the material determine how much acidic acid-base solution is absorbed per unit area of the material. The effectiveness of the pH neutralization causing the indicator solution to change color is dependent, however, upon surface area exposure and generally the thinner the porous substrate 12 the more sensitive the bacterial biological agent/toxin indicator 10. The other dimensions of the substrate 12 regarding surface area, i.e. excluding thickness, must only be sufficient to ensure visibility of the color change caused by pH neutralization.

With regard to this change in color it is noted that Phloxine B is specifically suggested partly because it changes from colorless to pink. The acidity of this solution ranges from 2.1–4.1. Bromophenol blue is also specifically suggested partly because it changes from yellow to blue-violet. The acidity of this solution ranges from 3.0–4.6. Both of these color changes are considered easily recognized and both acidity ranges are considered to be within the preferred range of 2–5 pH. Both of these solutions, moreover, are operative below the freezing point of water, which as mentioned previously, is considered desirable.

The foregoing is intended to provide one practiced in the art with the best known means of making and utilizing an embodiment in accordance with the principles relating to the present invention and is not to be construed in any manner as restrictive of said invention or the rights and privileges secured by Letters Patent for which I claim:

What is claimed is:

1. An anti-terrorist system, intended to prevent the transmission of live bacterial biological agents including *Bacillus antracis*, i.e. anthrax, and the toxins produced by said agents through the mail and to assist in the detection and identification of specific pieces of mail containing bacterial biological agents including *Bacillus antracis*, said system comprising:

at least one bacterial biological agent/toxin indicator mounted upon a wall of a mailing enclosure adapted for use in mailing materials;

said bacterial biological agent/toxin indicator possessing an appropriately porous substrate coated with an acidic acid-base solution which changes color in reaction to being neutralized by volatile bases including amines;

a window made of a substantially transparent material substantially contiguous with said wall;

said appropriately porous substrate coated with an acidic acid-base indicator solution being disposed by the mounting of said bacterial biological indicator upon a wall of said enclosure in communication with the interior of said mailing enclosure and interiorly adjacent said window;

whereby live bacterial biological agents including *Bacillus antracis* emitting gaseous amines and toxins produced by said agents inside said mailing enclosure are detected by observing, through said window, the change in color of the acidic acid-base solution coating upon said appropriately porous substrate resulting from pH neutralization.

2. An anti-terrorist system in accordance with claim 1 utilizing an acidic acid-base indicator solution coated upon said appropriately porous substrate without aqueous mediation and said bacterial biological indicator is operable below the freezing point of water.

3. An anti-terrorist system in accordance with claim 2 utilizing a halogenated xanthene dye as the acidic acid-base indicator solution coated upon said appropriately porous substrate of said bacterial biological indicator.

4. An anti-terrorist system in accordance with claim 2 utilizing a sulfonated hydroxyl-functional triphenylmethane dye as the acidic acid-base indicator solution coated upon said appropriately porous substrate of said bacterial biological indicator.

5. An anti-terrorist system in accordance with claim 1 having a machine readable code printed thereupon by which verification of the mailing enclosure can be automatically made by scanning said code.

6. An anti-terrorist system in accordance with claim 1 utilizing a box for said mailing enclosure.

7. An anti-terrorist system in accordance with claim 1 utilizing a window made of substantially transparent sheet material disposed over an aperture through said wall.

8. An anti-terrorist system in accordance with claim 1 utilizing an envelope possessing a fixed configuration with a perimeter having a recognizable top edge for said mailing enclosure.

9. An anti-terrorist system in accordance with claim 8 utilizing paper in construction of said envelope.

10. An anti-terrorist system in accordance with claim 8 having said porous substrate coated with acidic acid-base indicator solution disposed interiorly adjacent said window at a consistent positioning which regard to the perimeter of the envelope proximate the top edge of said envelope to facilitate reading by automatic scanning machines.

11. An anti-terrorist system in accordance with claim 10 having said appropriately porous substrate coated with acidic acid-base indicator solution affixed to said window made of substantially transparent sheet material.

12. An anti-terrorist system in accordance with claim 11 having an electronic fingerprint deposed thereupon by which verification of the mailing enclosure can be automatically made by scanning said electronic fingerprint.

13. An anti-terrorist system, intended to prevent the transmission of live bacterial biological agents including *Bacillus antracis*, i.e. anthrax, through the mail and to assist in the detection and identification of specific pieces of mail containing bacterial biological agents including *Bacillus antracis*, said system comprising:

at least one bacterial biological agent/toxin indicator mounted upon a wall of a mail enclosure adapted for use in enclosing mail;

said bacterial biological agent/toxin indicator possessing an appropriately porous substrate coated with an acidic acid-base solution which changes color in reaction to being neutralized by volatile bases including amines;

a window made of a substantially transparent material substantially contiguous with said wall;

said appropriately porous substrate coated with an acidic acid-base indicator solution being disposed by the mounting of said bacterial biological indicator upon a wall of said enclosure in communication with the interior of said mail enclosure and interiorly adjacent said window;

whereby live bacterial biological agents including *Bacillus antracis* emitting gaseous amines and toxins produced by said agents inside said mail enclosure are detected by observing, through said window, the change in color of the acidic acid-base solution coating upon said appropriately porous substrate resulting from pH neutralization.

14. An anti-terrorist system in accordance with claim 13 utilizing a window made of a substantially rigid transparent material.

15. An anti-terrorist system in accordance with claim 14 utilizing a plug style window possessing a cavity for disposition of said appropriately porous substrate coated with said acidic acid-base indicator solution.

16. An anti-terrorist system in accordance with claim 14 utilizing a mail receptacle as said enclosure.

17. An anti-terrorist system in accordance with claim 14 utilizing a transport container possessing handles as said enclosure intended to transport mail from a mail receptacle to a mail processing center.

18. An anti-terrorist system in accordance with claim 14 having at least one port upon one wall of said enclosure enabling the application of negative pressure to the interior of said enclosure.

19. An anti-terrorist system in accordance with claim 14 utilizing a substantially transparent rigid material for construction of said wall of said enclosure.

20. An anti-terrorist system, intended to prevent the transmission of live bacterial biological agents including *Bacillus antracis*, i.e. anthrax, through the mail and to assist in the detection and identification of specific pieces of mail containing bacterial biological agents including *Bacillus antracis*, said system comprising:

at least one bacterial biological agent/toxin indicator mounted upon a wall of a glove to be worn inside an enclosure containing mail;

said bacterial biological agent/toxin indicator possessing an appropriately porous substrate coated with an acidic acid-base solution which changes color in reaction to being neutralized by volatile bases including amines;

said appropriately porous substrate coated with an acidic acid-base indicator solution being disposed by the mounting of said bacterial biological indicator upon a wall of said glove in communication with the interior of enclosure containing mail;

whereby live bacterial biological agents including *Bacillus antracis* emitting gaseous amines and toxin produced by said agents inside said enclosure containing mail are detected by observing the change in color of the acidic acid-base solution coating upon said appropriately porous substrate resulting from pH neutralization.

21. An anti-terrorist system in accordance with claim 20 in which one said substrate coated with acidic acid-base indicator solution is affixed to the top of said glove.

22. An anti-terrorist system in accordance with claim 21 in which at least one said substrate coated with acidic acid-base indicator solution is affixed to the bottom of said glove.

23. An anti-terrorist system in accordance with claim 22 in which more than one said substrate coated with acidic acid-base indicator solution is each affixed to a finger of the glove.

* * * * *